United States Patent
Cushion et al.

(10) Patent No.: US 9,636,429 B2
(45) Date of Patent: May 2, 2017

(54) TRAY AND BRACKET SYSTEM AND RELATED METHODS

(71) Applicant: Symmetry Medical Manufacturing Inc., Warsaw, IN (US)

(72) Inventors: Robert Cushion, Manchester, NH (US); Jason Hawkes, Weare, NH (US)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 0 days.

(21) Appl. No.: 14/539,352

(22) Filed: Nov. 12, 2014

(65) Prior Publication Data

US 2015/0129524 A1    May 14, 2015

Related U.S. Application Data

(60) Provisional application No. 61/903,066, filed on Nov. 12, 2013.

(51) Int. Cl.
| | |
|---|---|
| *A47F 7/00* | (2006.01) |
| *A61L 2/00* | (2006.01) |
| *A61L 2/26* | (2006.01) |
| *A61B 50/34* | (2016.01) |
| *A61B 50/20* | (2016.01) |
| *A61B 50/33* | (2016.01) |

(52) U.S. Cl.
CPC .............. *A61L 2/00* (2013.01); *A61B 50/20* (2016.02); *A61B 50/33* (2016.02); *A61B 50/34* (2016.02); *A61L 2/26* (2013.01); *A61L 2202/182* (2013.01); *Y10T 29/49899* (2015.01)

(58) Field of Classification Search
CPC ... A61L 2/26; A61B 19/0256; A61B 19/0271; A61B 50/20; A61B 50/33
USPC .......................... 206/363, 370, 439, 477–483
See application file for complete search history.

(56) References Cited

U.S. PATENT DOCUMENTS

| | | | | |
|---|---|---|---|---|
| 3,890,459 | A | * | 6/1975 | Caveney ........................ 174/101 |
| 3,954,184 | A | * | 5/1976 | Mendenhall ................... 211/184 |
| 4,135,868 | A | | 1/1979 | Schainholz |
| 4,262,799 | A | * | 4/1981 | Perrett .......................... 206/363 |
| 4,798,292 | A | * | 1/1989 | Hauze ........................... 206/439 |
| 5,173,273 | A | | 12/1992 | Brewer |
| 5,215,726 | A | * | 6/1993 | Kudla et al. .................. 422/297 |
| 5,384,103 | A | | 1/1995 | Miller |
| 5,441,709 | A | * | 8/1995 | Berry, Jr. ...................... 422/297 |

(Continued)

*Primary Examiner* — Leslie A Nicholson, III
*Assistant Examiner* — Kimberley S Wright
(74) *Attorney, Agent, or Firm* — Hayes Soloway PC

(57) ABSTRACT

A bracket and tray connection system includes a tray with a plurality of connector holes positioned therein, wherein the tray has an upper surface. A bracket has a base surface positioned proximate to an upper surface of the tray. At least one fastening tab is formed on the base surface of the bracket, wherein the fastening tab extends away from the base surface and through at least one of the connector holes within the tray. An interior corner pocket is formed by the fastening tab and located at least partially between the base surface and the fastening tab. An exterior corner of at least one of the connector holes is positioned with the interior corner pocket. A retainer structure is formed on the base surface of the bracket, wherein the retainer structure engages with the tray to retain the exterior corner positioned within the interior corner pocket.

20 Claims, 12 Drawing Sheets

(56) References Cited

U.S. PATENT DOCUMENTS

| | | | |
|---|---|---|---|
| 5,492,671 A | 2/1996 | Krafft | |
| 5,599,512 A | 2/1997 | Latulippe et al. | |
| 5,628,970 A * | 5/1997 | Basile et al. | 422/297 |
| 5,681,539 A * | 10/1997 | Riley | 422/300 |
| 5,759,502 A * | 6/1998 | Spencer et al. | 422/300 |
| 5,827,487 A * | 10/1998 | Holmes | 422/297 |
| 6,099,812 A * | 8/2000 | Allen et al. | 422/300 |
| 6,193,932 B1 * | 2/2001 | Wu et al. | 422/28 |
| 6,244,447 B1 * | 6/2001 | Frieze et al. | 211/85.13 |
| 6,331,280 B1 * | 12/2001 | Wood | 422/300 |
| 6,382,575 B1 | 5/2002 | Frush et al. | |
| 6,436,357 B1 * | 8/2002 | Frieze et al. | 422/300 |
| 6,468,482 B1 * | 10/2002 | Frieze et al. | 422/300 |
| 6,827,913 B2 | 12/2004 | Wood | |
| 6,896,149 B1 * | 5/2005 | Berry, III | 220/4.28 |
| 6,969,498 B1 * | 11/2005 | Riley | 422/300 |
| 7,021,485 B1 * | 4/2006 | Baker et al. | 220/326 |
| D535,754 S | 1/2007 | Bennison | |
| 7,341,148 B2 * | 3/2008 | Bettenhausen et al. | 206/370 |
| 7,544,336 B2 | 6/2009 | Powell | |
| 7,601,312 B2 * | 10/2009 | Riley et al. | 422/300 |
| 7,717,264 B2 * | 5/2010 | Bettenhausen et al. | 206/370 |
| 7,748,529 B2 | 7/2010 | Foreman et al. | |
| 7,861,860 B2 * | 1/2011 | Bettenhausen et al. | 206/370 |
| 8,069,998 B2 * | 12/2011 | Thomas | 211/85.13 |
| 8,075,849 B2 | 12/2011 | Riley | |
| 8,267,246 B2 * | 9/2012 | Bettenhausen et al. | 206/363 |
| 8,272,508 B2 * | 9/2012 | Bettenhausen et al. | 206/370 |
| 8,485,567 B1 * | 7/2013 | Meuchel | 292/137 |
| 8,827,088 B1 * | 9/2014 | Krause et al. | 211/85.13 |
| 2002/0071799 A1 | 6/2002 | Wood | |
| 2002/0074253 A1 | 6/2002 | Allen et al. | |
| 2003/0198581 A1 | 10/2003 | Sweet, II et al. | |
| 2005/0249651 A1 * | 11/2005 | Riley | 422/300 |
| 2006/0191939 A1 * | 8/2006 | Baker et al. | 220/326 |
| 2006/0213794 A1 | 9/2006 | Foreman et al. | |
| 2006/0266666 A1 * | 11/2006 | Bettenhausen et al. | 206/370 |
| 2007/0009408 A1 * | 1/2007 | Riley | 422/300 |
| 2007/0134142 A1 | 6/2007 | Riley | |
| 2007/0144926 A1 * | 6/2007 | Bettenhausen et al. | 206/363 |
| 2007/0205123 A1 * | 9/2007 | Bettenhausen et al. | 206/363 |
| 2008/0149512 A1 * | 6/2008 | Dane | 206/370 |
| 2008/0314789 A1 * | 12/2008 | Thomas | 206/572 |
| 2009/0146032 A1 * | 6/2009 | Bettenhausen et al. | 248/220.31 |
| 2010/0176016 A1 | 7/2010 | Pell | |
| 2012/0085720 A1 * | 4/2012 | Bettenhausen et al. | 211/85.13 |
| 2013/0319888 A1 * | 12/2013 | Birkbeck et al. | 206/370 |
| 2014/0083886 A1 * | 3/2014 | Winterrowd et al. | 206/370 |

* cited by examiner

300

A tray having a plurality of connector holes positioned therein is provided, wherein the tray has an upper surface and a lower surface — 302

A bracket is engaged to at least one of the plurality of connector holes of the tray, wherein the bracket has a base surface and at least one fastening tab formed on the base surface of the bracket, wherein the at least one fastening tab extends away from the base surface and through at least one of the plurality of connector holes within the tray, whereby the base surface is positioned proximate to an upper surface of the tray, whereby an exterior corner of at least one of the plurality of connector holes is positioned proximate to an interior corner pocket formed by the at least one fastening tab and located at least partially between the base surface and the at least one fastening tab — 304

The bracket is retained to the tray with a retainer structure formed on the base surface of the bracket, wherein the retainer structure engages with the tray to retain the exterior corner positioned within the interior corner pocket — 306

FIG. 12

TRAY AND BRACKET SYSTEM AND RELATED METHODS

CROSS REFERENCE TO RELATED APPLICATION

This application claims benefit of U.S. Provisional Application Ser. No. 61/903,066, entitled, "Bracket with Retainer Mechanism System and Related Methods" filed Nov. 12, 2013, the entire disclosure of which is incorporated herein by reference.

FIELD OF THE DISCLOSURE

The present disclosure is generally related to brackets and more particularly is related to a tray and bracket system and related methods.

BACKGROUND OF THE DISCLOSURE

There exists in the prior art various retainers and accessories for fixing the positions of articles of one kind or another. These include hooks, pegs, clips, brackets, etc. Such retainers may be used in a wide variety of applications. For example, they are commonly used in the medical field to fix the positions of various surgical instruments, devices and prostheses while those articles are being transported, sterilized and processed in one way or another.

Medical instruments are often transported in trays. Prior to use, such instruments are placed in the tray and subjected to sterilization. To improve the circulation of steam throughout the tray, the tray bottom wall and perhaps also the side wall are usually perforated. In order to maintain a separation between the various instruments in the tray, the instruments are supported or retained by posts, brackets or other retainers anchored to the tray. Following sterilization, the tray full of instruments may be transported to an operating room and placed close to a surgical team whose members may withdraw the instruments from the tray as needed for the particular surgical procedure being performed. Usually, the instruments are selectively arranged or organized in the tray so that they can be picked from the tray in the order in which they are needed for the particular procedure.

Sterilization trays may come in a variety of configurations, such that they can hold a number of different instruments. While the companies that require sterilization trays may assemble bracketry themselves, it often is a cumbersome process, since it requires positioning and connecting each bracket, which often has multiple parts. Additionally, once the bracket is assembled, it may become necessary to remove the bracket from the tray to properly sterilize it. Bracketry that uses multiple pieces can be time consuming to assemble and disassemble, which results in inefficiencies with using the tray. These inefficiencies may waste time and money.

Thus, a heretofore unaddressed need exists in the industry to address the aforementioned deficiencies and inadequacies.

SUMMARY OF THE DISCLOSURE

Embodiments of the present disclosure provide a bracket and tray connection system and related methods. Briefly described, in architecture, one embodiment of the system, among others, can be implemented as follows. A tray has a plurality of connector holes positioned therein, wherein the tray has an upper surface and a lower surface. A bracket has a base surface positioned proximate to an upper surface of the tray. At least one fastening tab is formed on the base surface of the bracket, wherein the at least one fastening tab extends away from the base surface and through at least one of the plurality of connector holes within the tray. An interior corner pocket is formed by the at least one fastening tab and located at least partially between the base surface and the at least one fastening tab, wherein an exterior corner of at least one of the plurality of connector holes is positioned with the interior corner pocket. A retainer structure is formed on the base surface of the bracket, wherein the retainer structure engages with the tray to retain the exterior corner positioned within the interior corner pocket.

The present disclosure can also be viewed as providing a bracket for supporting instruments on a tray. Briefly described, in architecture, one embodiment of the bracket, among others, can be implemented as follows. The bracket includes a base and an instrument holding portion extending from the base. A base surface is positioned on an opposing side of the base from the instrument holding portion. At least one fastening tab is formed on the base surface, wherein the at least one fastening tab extends away from the base surface. An interior corner pocket is formed by the at least one fastening tab and located at least partially between the base surface and the at least one fastening tab. A retainer structure is formed on the base surface of the bracket.

The present disclosure can also be viewed as providing methods of securing a bracket to a tray. In this regard, one embodiment of such a method, among others, can be broadly summarized by the following steps: providing a tray having a plurality of connector holes positioned therein, wherein the tray has an upper surface and a lower surface; engaging a bracket to at least one of the plurality of connector holes of the tray, the bracket having a base surface and at least one fastening tab formed on the base surface of the bracket, wherein the at least one fastening tab extends away from the base surface and through at least one of the plurality of connector holes within the tray, whereby the base surface is positioned proximate to an upper surface of the tray, whereby an exterior corner of at least one of the plurality of connector holes is positioned proximate to an interior corner pocket formed by the at least one fastening tab and located at least partially between the base surface and the at least one fastening tab; and retaining the bracket to the tray with a retainer structure formed on the base surface of the bracket, wherein the retainer structure engages with the tray to retain the exterior corner positioned within the interior corner pocket.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 12 is a flowchart illustrating a method of securing a bracket to a tray, in accordance with a fourth exemplary embodiment of the disclosure.

DETAILED DESCRIPTION

Figure 1:
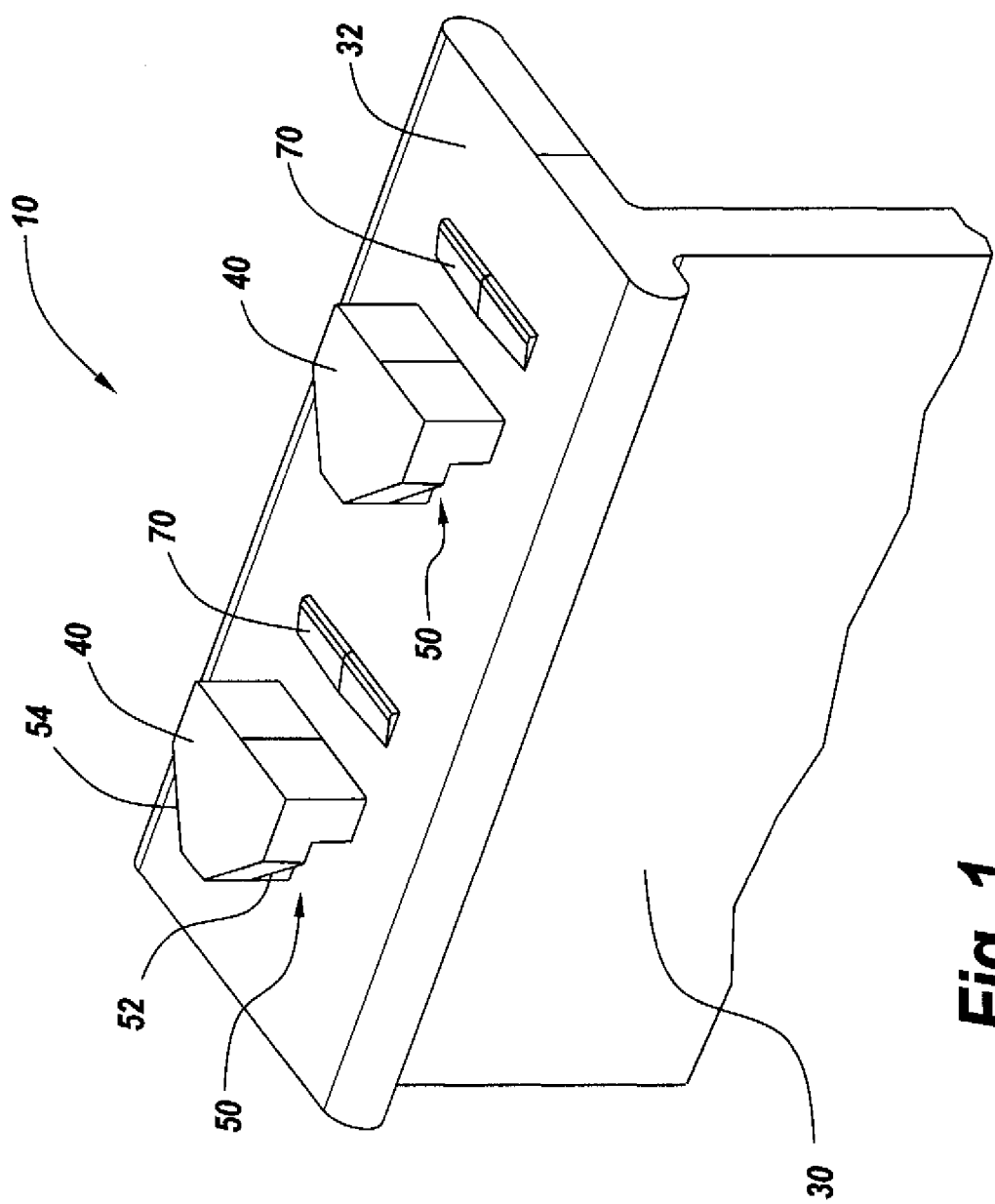
FIG. 1 is a plan view illustration of a bracket of the bracket system, in accordance with a first exemplary embodiment of the present disclosure.
Figure 2:
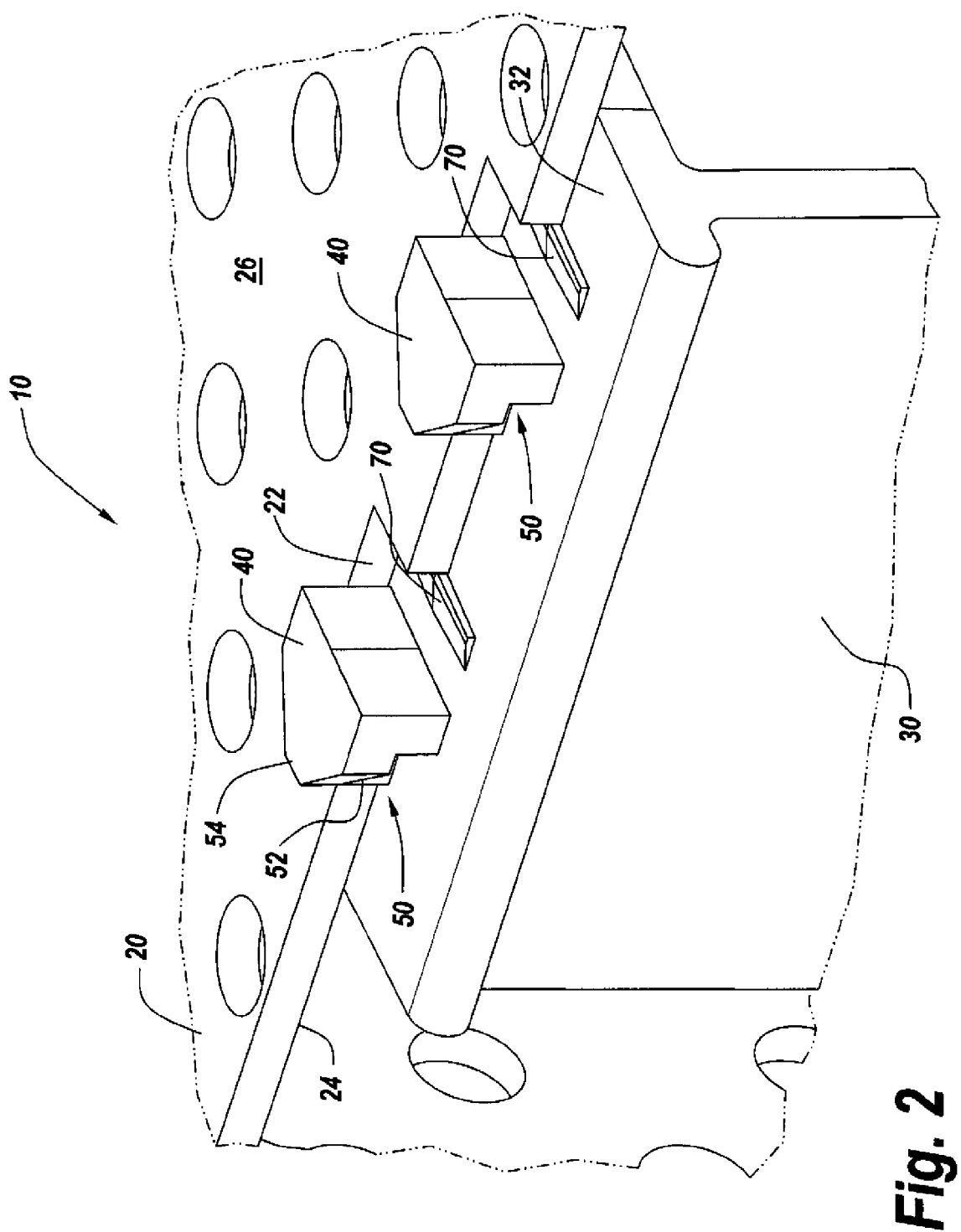
FIG. 2 is a partial cross-sectional view illustration of a bracket connected to the tray of the bracket system, in accordance with the first exemplary embodiment of the present disclosure.
Figure 3:
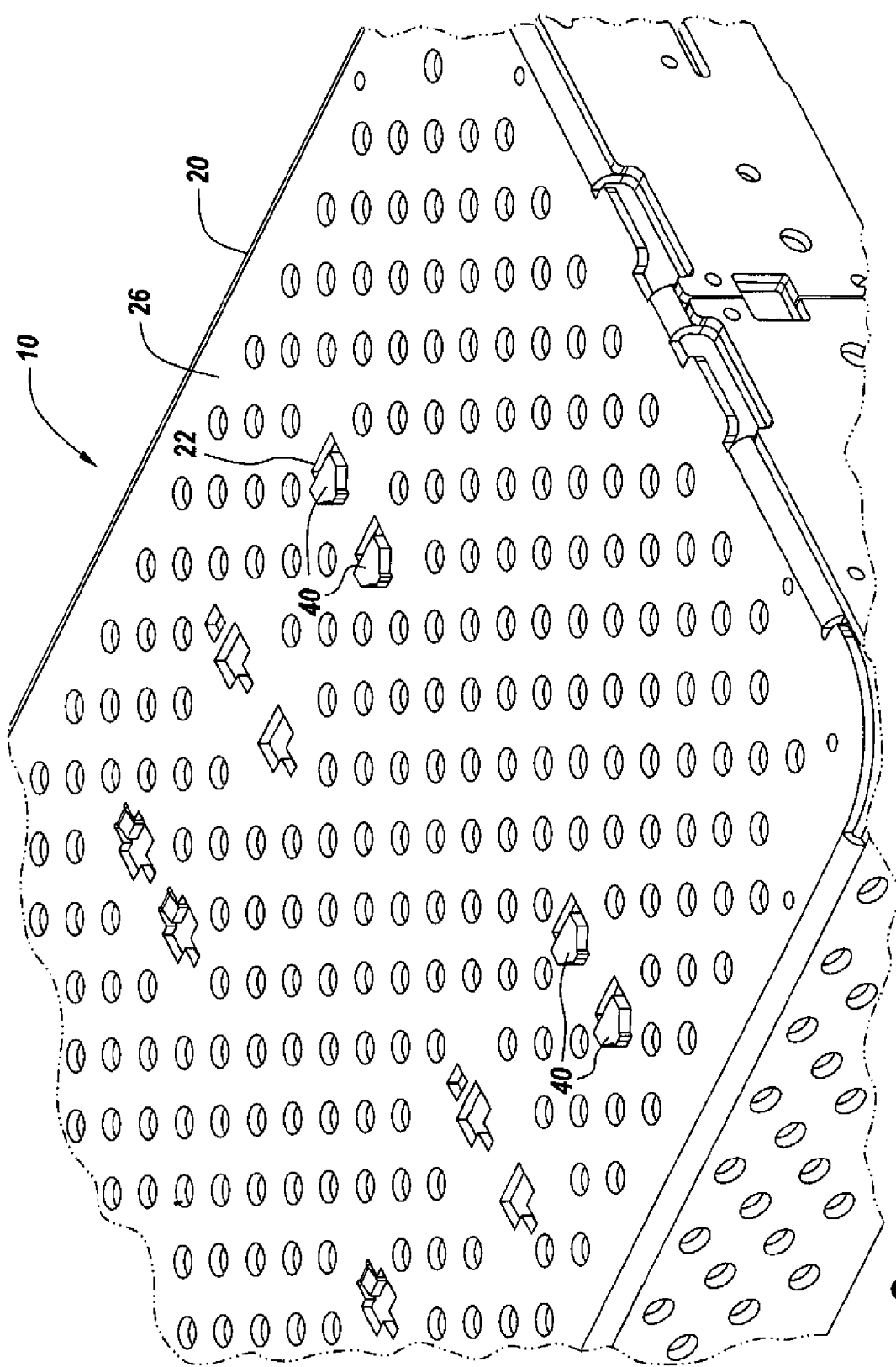
FIG. 3 is a bottom plan view illustration of a bracket connected to the tray of the bracket system, in accordance with the first exemplary embodiment of the present disclosure.
Figure 4:
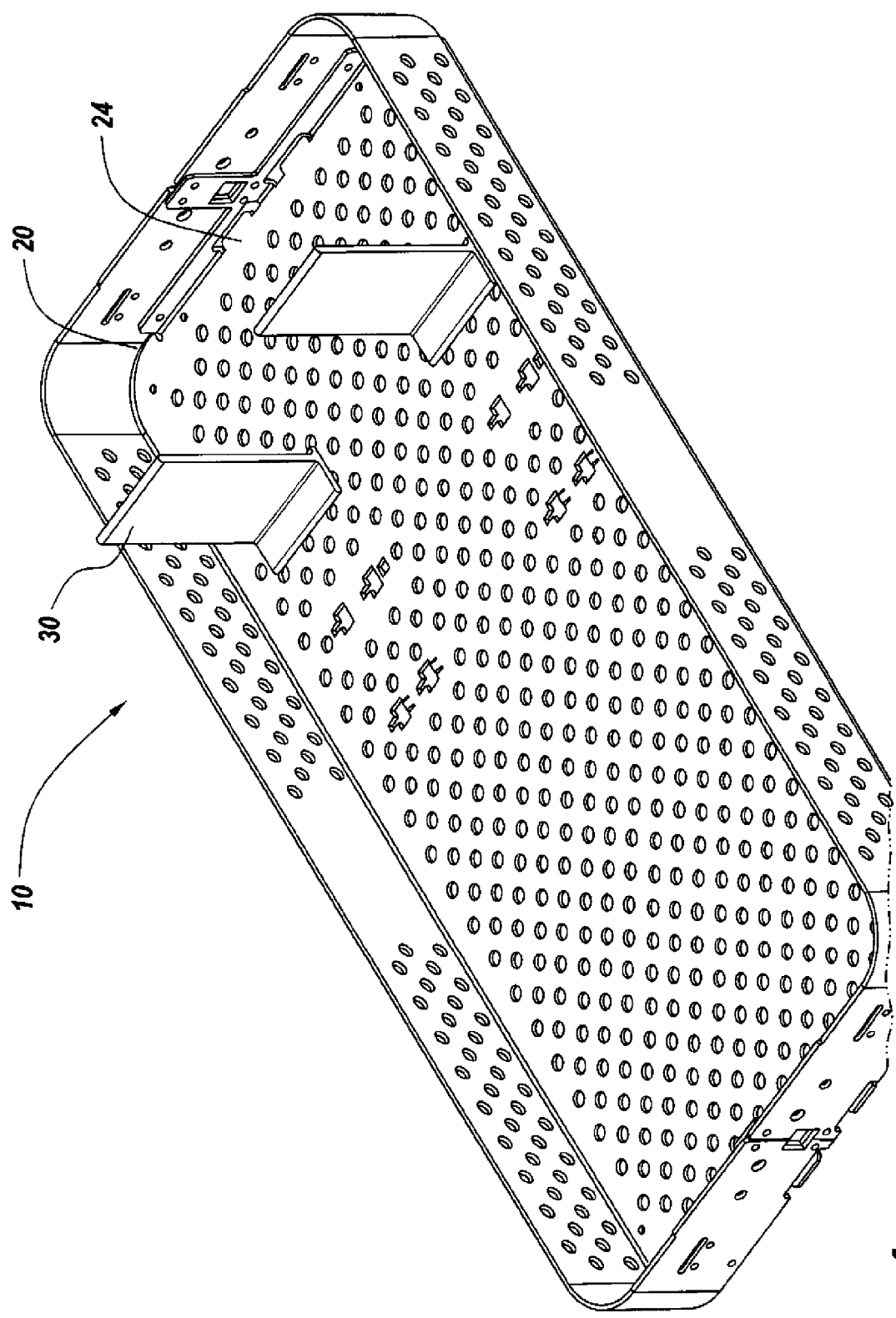
FIG. 4 is a top plan view illustration of a bracket connected to the tray of the bracket system, in accordance with the first exemplary embodiment of the present disclosure.

FIG. 1 is a plan view illustration of a bracket 30 of the bracket system 10, in accordance with a first exemplary embodiment of the present disclosure. FIG. 2 is a partial cross-sectional view illustration of a bracket 30 connected to the tray 20 of the bracket system 10, in accordance with the first exemplary embodiment of the present disclosure. FIG. 3 is a bottom plan view illustration of a bracket 30 connected to the tray 20 of the bracket system 10, in accordance with the first exemplary embodiment of the present disclosure. FIG. 4 is a top plan view illustration of a bracket 30 connected to the tray 20 of the bracket system 10, in accordance with the first exemplary embodiment of the present disclosure.

With respect to FIGS. 1-4, the bracket system 10, which may be referred to herein as 'system 10' includes a tray 20 having a plurality of connector holes 22 positioned therein, wherein the tray 20 has an upper surface 24 and a lower surface 26. A bracket 30 has a base surface 32 positioned proximate to an upper surface 24 of the tray 20. At least one fastening tab 40 is formed on the base surface 32 of the bracket 30, wherein the at least one fastening tab 40 extends away from the base surface 32 and through at least one of the plurality of connector holes 22 within the tray 20. An interior corner pocket 50 is formed by the at least one fastening tab 40 and is located at least partially between the base surface 32 and the at least one fastening tab 30, wherein an exterior corner 60 (Shown in FIG. 5) of at least one of the plurality of connector holes 22 is positioned with the interior corner pocket 50. A retainer structure 70 is formed on the base surface 32 of the bracket 30, wherein the retainer structure 70 engages with the tray 20 to retain the exterior corner 60 positioned within the interior corner pocket 50.

The tray 20 may have any size or dimension, and may commonly include tray walls positioned around a substantially planar middle section. The tray 20 includes a plurality of connector holes 22 positioned within the tray 20, and may include a plurality of other holes for allowing the ingress and egress of sterilization fluid or materials during a sterilization process. The connector holes 22 may be positioned within the tray 20 and between the upper surface 24 and the lower surface 26, which are positioned in opposing directions from one another.

The bracket 30 is a rigid, partially rigid, or slightly flexible structure that is capable of holding a medical instrument, or other implement that is placed within the tray 20. While not shown, the bracket 30 may include any features or structures for holding the medical instrument. The bracket 30 has a base surface 32 that is positioned proximate to an upper surface 24 of the tray 20, such as in an abutting position on the upper surface 24. The bracket 30 can, of course, be removed from a location on the tray 20, in which case the base surface 32 of the bracket 30 would not be positioned proximate to the upper surface 24.

A fastening tab 40, or more commonly a plurality of fastening tabs 40, is formed on the base surface 32 of the bracket 30 and extends away from the base surface 32. The fastening tab 40 allows the bracket 30 to be connected to the tray 20, by engagement between the fastening tab 40 with the connector hole 22. This connection between the fastening tab 40 the connector hole 22 within the tray 20 is removable, such that the bracket 30 can be removed from the tray 20 when necessary, such as when cleaning of the bracket 30 or tray 20 is required. The fastening tab 40 may have a variety of shapes and sizes, but may generally be sized smaller than the base surface 32 of the bracket 30, such that when the fastening tab 40 is connected with the connector hole 22, the base surface 32 sits flush on the upper surface 24 of the tray 20.

Figure 5:
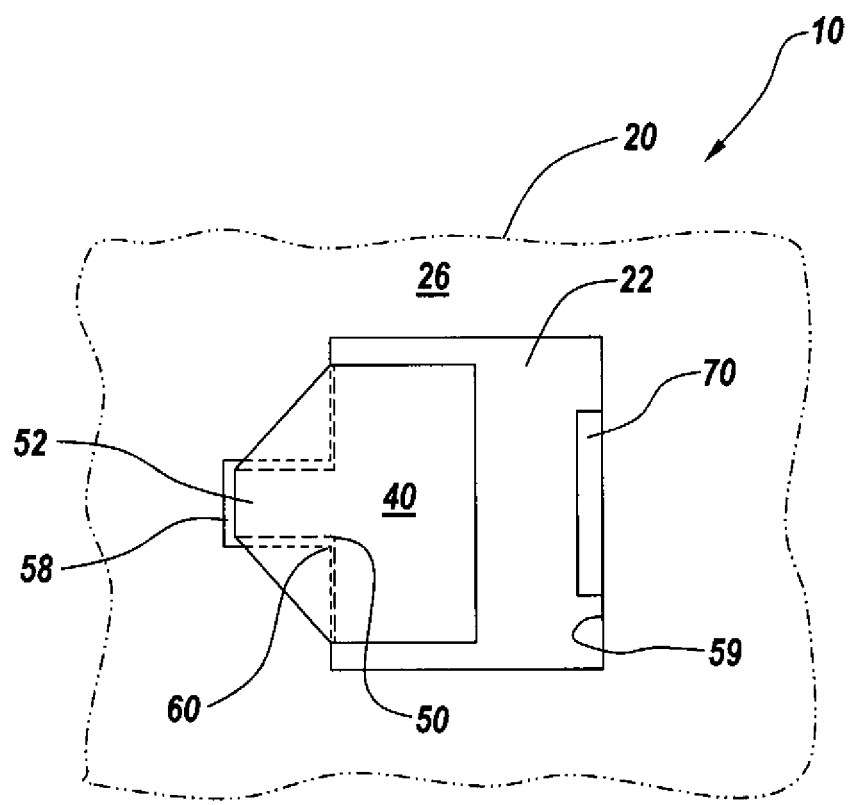
FIG. 5 is a bottom view illustration of the bracket system, in accordance with the first exemplary embodiment of the present disclosure.

While the fastening tab 40 may include various structures, at least one interior corner pocket 50 is formed by the fastening tab 40. This interior corner pocket 50 may be characterized as a structure of the fastening tab 40 where three or more surfaces intersect at an angle that is less than 180°. As is shown in FIGS. 1-2 and FIG. 5, the interior corner pocket 50 may include three surfaces that intersect at 90° angles relative to one another. It may be common for each fastening tab 40 to have two interior corner pockets 50 that are formed on opposing sides of a central wall 52, whereby opposing sides of the central wall 52 each form one of the three sides of the interior corner pocket 50. A top wall 54 may be positioned at an end of the fastening tab 40 and connected to the central wall 52, and act as another side for the interior corner pocket 50. In other words, the fastening tab 40 may include a T-shaped wall with a covering thereon, wherein the interior corner pocket(s) 50 are formed between the leg and arms of the T-shaped wall and the covering thereon. The interior corner pocket 50 is located at least partially between the base surface 32 and the at least one fastening tab 30.

The interior corner pocket 50 may engage with an exterior corner 60 of at least one of the plurality of connector holes 22 of the tray 20. In other words, the connector holes 22 may have a cutout T-shape, whereby the leg of the T-shape can receive the central wall 52 of the fastening tab 40. The exterior corners 60, e.g., the sides of the connector holes 22 forming the leg cutout of the T-shape, can be sized to fit within the interior corner pockets 50 when the fastening tab 40 is engaged with the connector hole 22.

A retainer structure 70 is also formed on the base surface 32 of the bracket 30. The retainer structure 70 engages with the tray 20 to retain the exterior corner 60 positioned within the interior corner pocket 50. For example, the retainer structure 70 may include a positive ramp extending from the base surface 32, which makes contact with a rear sidewall of the connector hole 22 when the fastening tab 40 is positioned within the connector hole 22, as is best shown in FIG. 2. The retainer structure 70 may prevent the fastening tab 40 from moving within the connector hole 22, thereby keeping the exterior corners 60 of the tray 20 positioned within the interior corner pockets 50. In other words, the retainer structure 70 can be used to lock the fastening tab 40 within the connector hole 22. Other designs for the retainer structure are available, as is discussed relative to FIGS. 6-11.

FIG. 5 is a bottom view illustration of the bracket system 10, in accordance with the first exemplary embodiment of the present disclosure. In particular, FIG. 5 depicts the fastening tab 40 positioned within the connector hole 22 in an engaged position. The connector hole 22 is depicted being within an exemplary section of the tray 20. Shown in broken lines, the exterior corners 60 of the connector hole 22 are positioned substantially abutting with the interior corner pockets 50 of the fastening tab 40. It can be seen that the central wall 52 of the fastening tab 40 is positioned within the leg 58 of the T-shaped cutout of the connector hole 22. In this position, the contact between the exterior corner 60 and the interior corner pockets 50 may prevent lateral movement of the fastening tab 40, and thus, the bracket 30. Linear movement of the fastening tab 40 within the connector hole 22 is prevented by the retainer structure 70 (shown as a positive ramp) that makes contact with a rear wall 59 of the connector hole 22.

Figure 6:
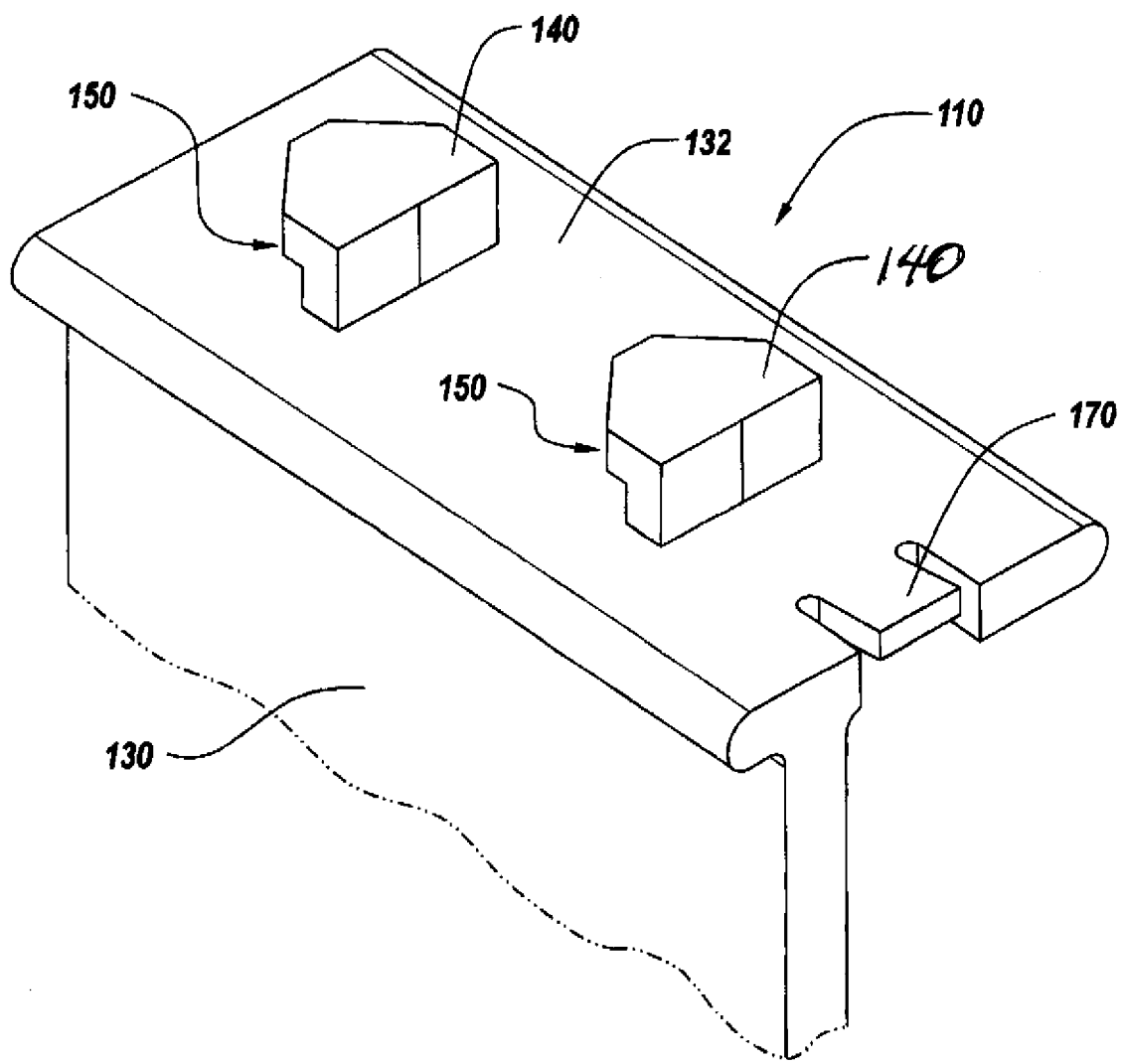
FIG. 6 is a plan view illustration of a bracket of the bracket system, in accordance with a second exemplary embodiment of the present disclosure.
Figure 7:
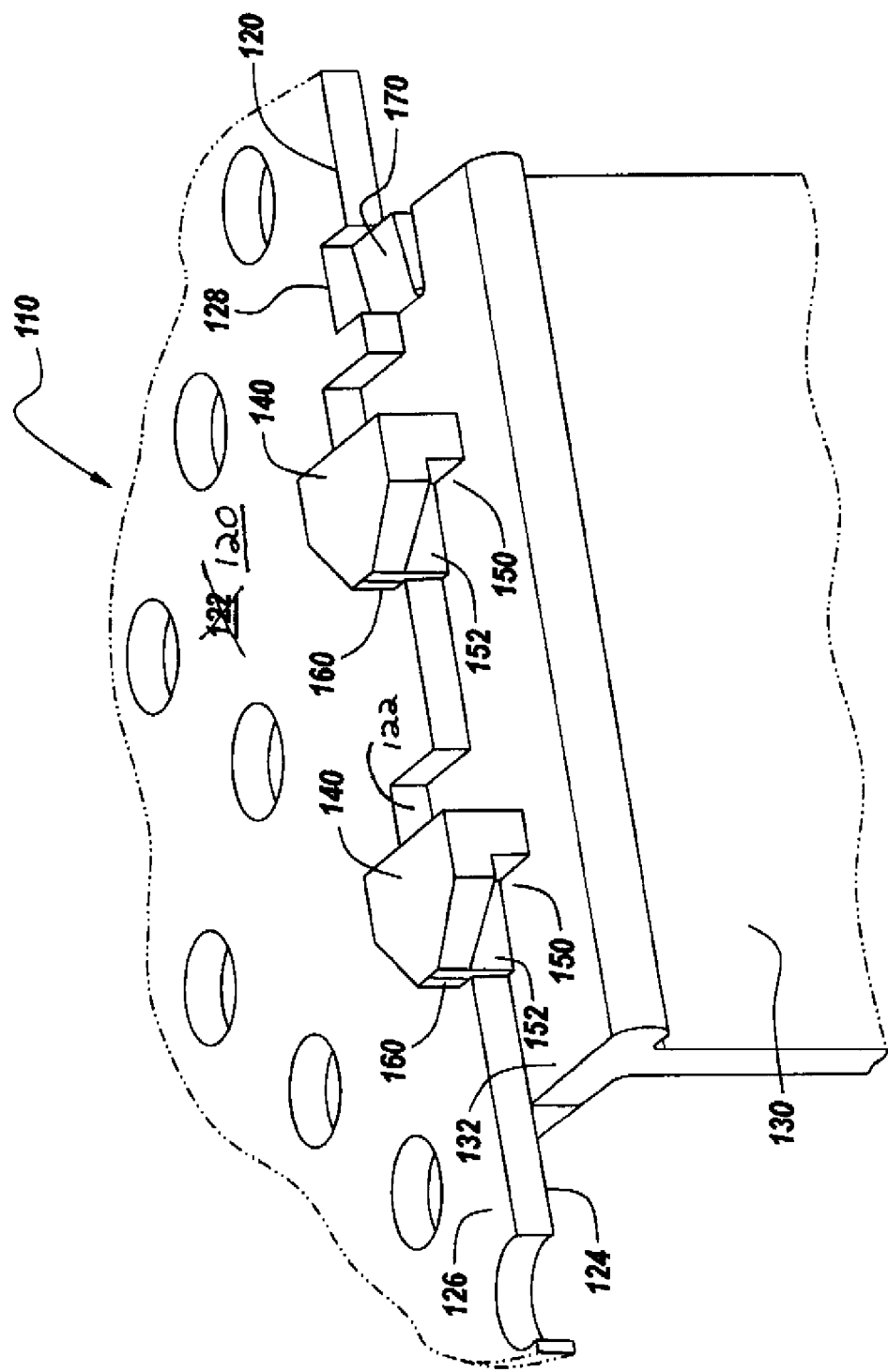
FIG. 7 is a partial cross-sectional view illustration of a bracket connected to the tray of the bracket system, in accordance with the second exemplary embodiment of the present disclosure.
Figure 8:
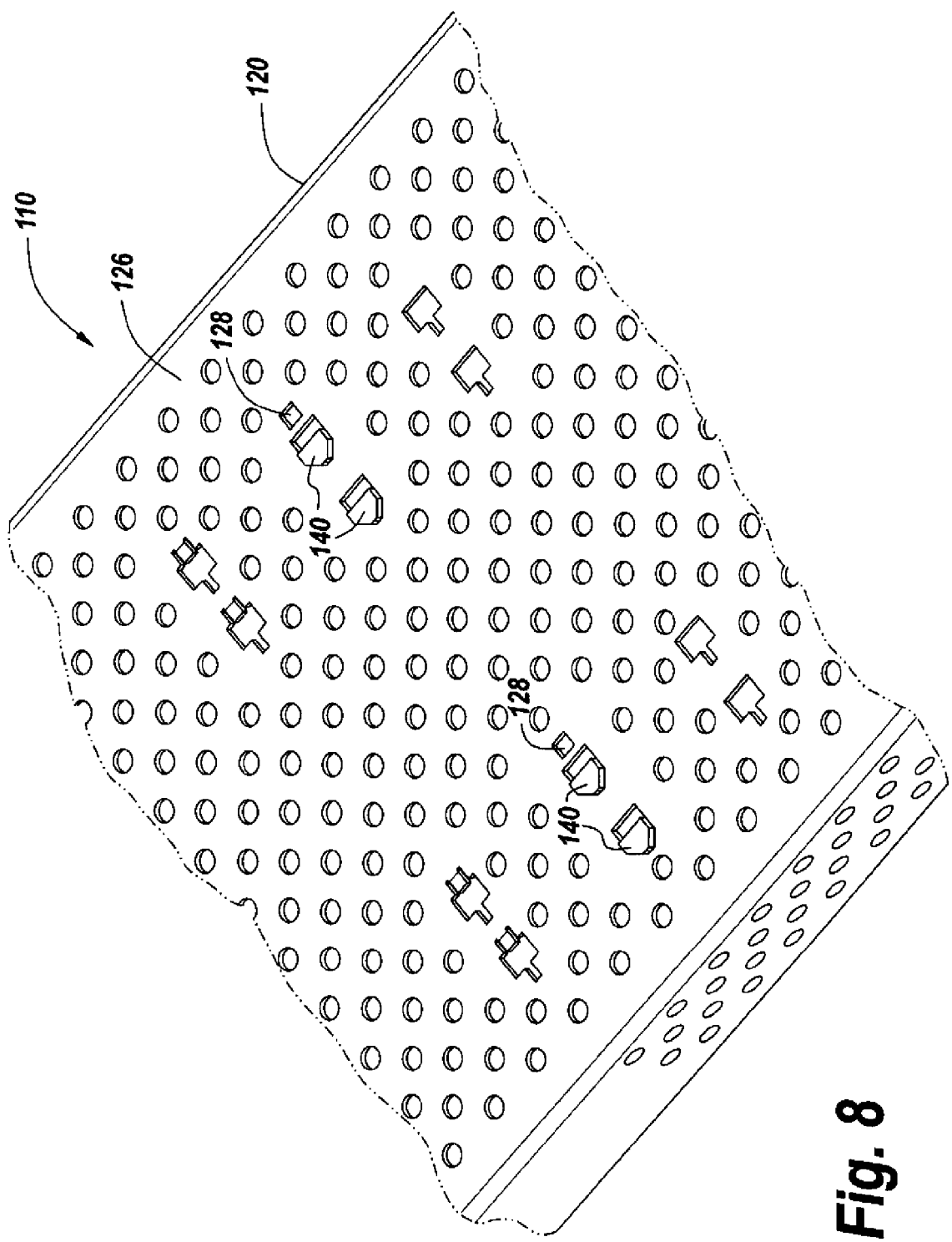
FIG. 8 is a bottom plan view illustration of a bracket connected to the tray of the bracket system, in accordance with the second exemplary embodiment of the present disclosure.

FIG. 6 is a plan view illustration of a bracket 130 of the bracket system 110, in accordance with a second exemplary embodiment of the present disclosure. FIG. 7 is a partial cross-sectional view illustration of the bracket 130 connected to the tray 120 of the bracket system 110, in accordance with the second exemplary embodiment of the present disclosure. FIG. 8 is a bottom plan view illustration of the bracket 130 connected to the tray 120 of the bracket system 110, in accordance with the second exemplary embodiment of the present disclosure. The bracket system 110 of FIGS. 6-8 may be substantially similar to the bracket system 10 of FIGS. 1-5 and it may include any of the features, components, or functions disclosed relative to any embodiment of this disclosure.

With respect to FIGS. 6-8, the bracket system 110, which may be referred to herein as 'system 110' includes a tray 120 having a plurality of connector holes 122 positioned therein, wherein the tray 120 has an upper surface 124 and a lower surface 126. A bracket 130 has a base surface 132 positioned proximate to an upper surface 124 of the tray 120. At least one fastening tab 140 is formed on the base surface 132 of the bracket 130, wherein the at least one fastening tab 140 extends away from the base surface 132 and through at least one of the plurality of connector holes 122 within the tray 120. An interior corner pocket 150 is formed by the at least one fastening tab 140 and is located at least partially between the base surface 132 and the at least one fastening tab 140, wherein an exterior corner 160 of at least one of the plurality of connector holes 122 is positioned with the interior corner pocket 150. A retainer structure 170 is formed on the base surface 132 of the bracket 130, wherein the retainer structure 170 engages with the tray 120 to retain the exterior corner 160 positioned within the interior corner pocket 150.

The bracket 130, the fastening tab 140, the interior corner pockets 150, and the exterior corners 160 of the system 110 may be substantially similar or the same as is disclosed relative to FIGS. 1-5. FIG. 7 shows the engagement between the fastening tab 140 and the connector hole 122, whereby the central wall 152, a back wall 153 and the top wall 154 form the interior corner pocket 150 that receives the exterior corner 160 of the connector hole 122. The central wall 152 and the back wall 153 may each be planar and may intersect with one another at an angle. Further, the central wall 152 and the back wall 153 may each be perpendicular to the base surface. The tray 120 may be substantially similar as well, but may include a retainer hole 128 that is formed within the tray 120. The retainer hole 128 may receive the retainer structure 170 when the fastening tab 140 is engaged with the connector hole 122. The retainer structure 170 may include a flexible tab that extends from the bracket 130 upwardly, above the base surface 132 of the bracket. The retainer structure 170 may be biasable towards the top of the bracket 130, such that it can spring or be resiliently moved into the retainer hole 128 of the tray 120 when the fastening tab 140 is engaged with the connector hole 122. Unlike the retainer structure 70 of FIGS. 1-5, which uses a retainer structure 70 for each fastening tab 40, the retainer structure 170 of FIGS. 6-8 may use a single retainer structure 170 for two or more fastening tabs 140.

Figure 9:
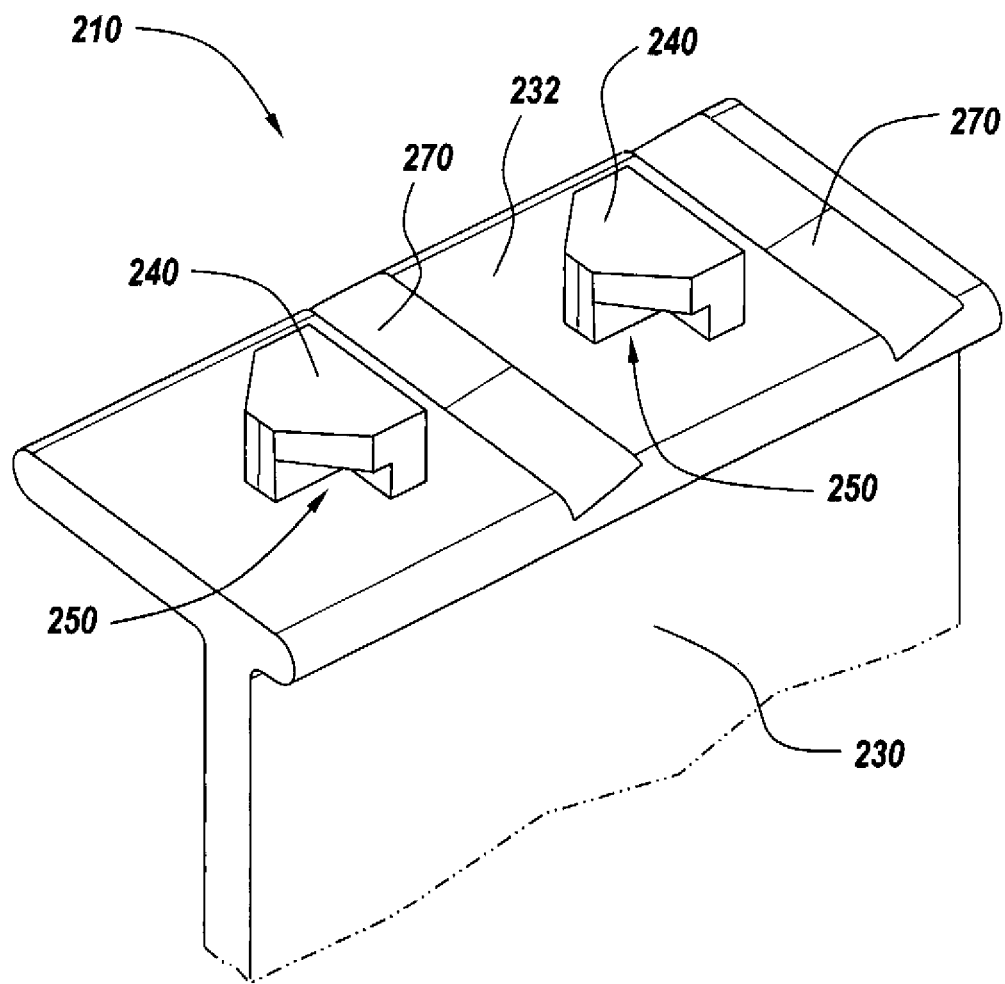
FIG. 9 is a plan view illustration of a bracket of the bracket system, in accordance with a third exemplary embodiment of the present disclosure.
Figure 10:
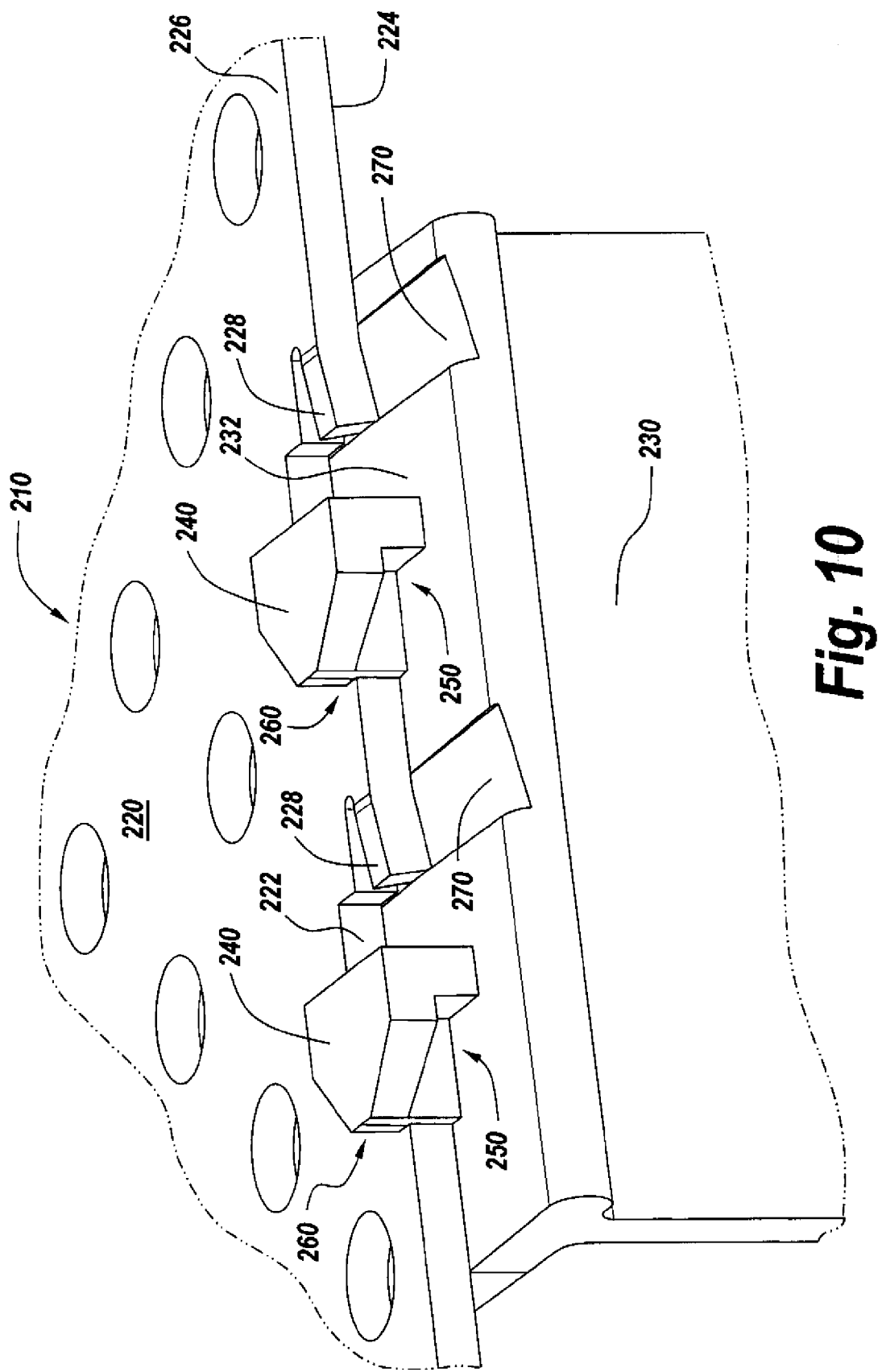
FIG. 10 is a partial cross-sectional view illustration of a bracket connected to the tray of the bracket system, in accordance with the third exemplary embodiment of the present disclosure.
Figure 11:
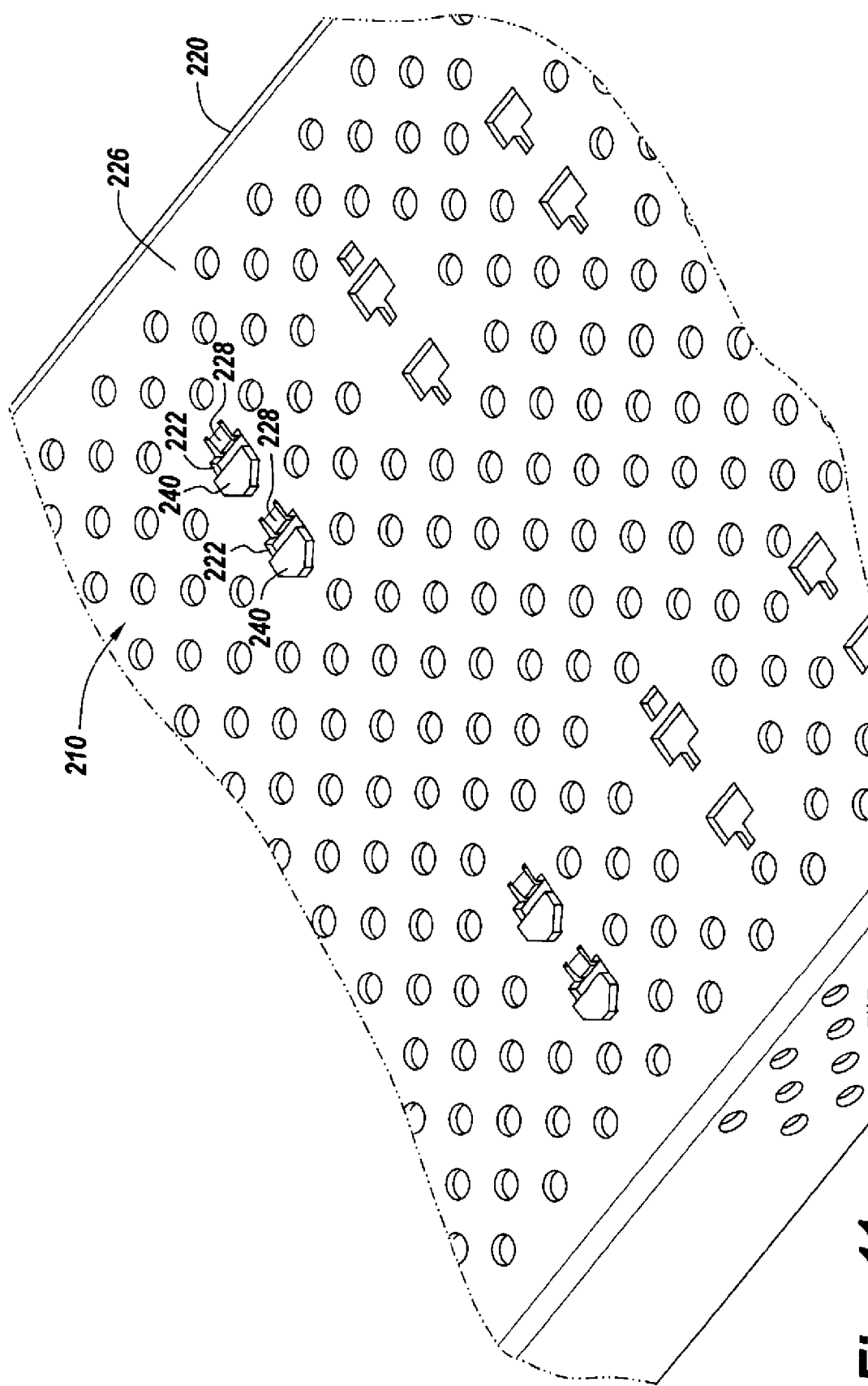
FIG. 11 is a bottom plan view illustration of a bracket connected to the tray of the bracket system, in accordance with the third exemplary embodiment of the present disclosure.

FIG. 9 is a plan view illustration of a bracket 230 of the bracket system 210, in accordance with a third exemplary embodiment of the present disclosure. FIG. 10 is a partial cross-sectional view illustration of a bracket 230 connected to the tray 220 of the bracket system 210, in accordance with the third exemplary embodiment of the present disclosure. FIG. 11 is a bottom plan view illustration of a bracket 230 connected to the tray 220 of the bracket system 210, in accordance with the third exemplary embodiment of the present disclosure. The bracket system 210 of FIGS. 9-11 may be substantially similar to the bracket system 10 of FIGS. 1-5 and it may include any of the features, components, or functions disclosed relative to any embodiment of this disclosure.

With respect to FIGS. 9-11, the bracket system 210, which may be referred to herein as 'system 210' includes a tray 220 having a plurality of connector holes 222 positioned therein, wherein the tray 220 has an upper surface 224 and a lower surface 226. A bracket 230 has a base surface 232 positioned proximate to an upper surface 224 of the tray 220. At least one fastening tab 240 is formed on the base surface 232 of the bracket 230, wherein the at least one fastening tab 240 extends away from the base surface 232 and through at least one of the plurality of connector holes 222 within the tray 220. An interior corner pocket 250 is formed by the at least one fastening tab 240 and is located at least partially between the base surface 232 and the at least one fastening tab 230, wherein an exterior corner 260 of at least one of the plurality of connector holes 222 is positioned with the interior corner pocket 250. A retainer structure 270 is formed on the base surface 232 of the bracket 230, wherein the retainer structure 270 engages with the tray 220 to retain the exterior corner 260 positioned within the interior corner pocket 250.

The bracket 230, the fastening tab 240, the interior corner pockets 250, and the exterior corners 260 of the system 210 may be substantially similar or the same as is disclosed relative to FIGS. 1-5. The tray 220 may be substantially similar to the tray 20 of FIGS. 1-5, but may include a retainer tab 228 that is formed within the tray 220 and extends towards the upper surface 224 of the tray 220. The retainer tab 228 may engage with the retainer structure 270 when the fastening tab 240 is engaged with the connector hole 222. The retainer structure 270 may be a negative ramp within the bracket 230 that extends into the base surface 232 of the bracket 230. The retainer tab 228 may be biasable towards the interior of the retainer structure 270, such that it can spring or be resiliently moved into the retainer structure 270 when the fastening tab 240 is engaged with the connector hole 222. Any number of retainer structure 270 and retainer tabs 228 may be used with a single bracket 230.

One of the many benefits that the present disclosure provides is the ability to efficiently manufacture and build medical sterilization systems for the medical industry. Instead of having customers build modular medical sterilization trays, a worker can quickly assemble the disclosed invention herein and provide a completed product to the customer. While the brackets 230 may be left engaged with the tray 220 for the life of the system 210, the customer has the option to remove the brackets 230 if necessary, such as when the brackets 230 need a thorough cleaning or if a bracket 230 is damaged.

FIG. 12 is a flowchart 300 illustrating a method of securing a bracket to a tray, in accordance with a fourth exemplary embodiment of the disclosure. It should be noted that any process descriptions or blocks in flow charts should be understood as representing modules, segments, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown at block 302, a tray having a plurality of connector holes positioned therein is provided, wherein the tray has an upper surface and a lower surface. A bracket is engaged to at least one of the plurality of connector holes of the tray, wherein the bracket has a base surface and at least one fastening tab formed on the base surface of the bracket, wherein the at least one fastening tab extends away from the base surface and through at least one of the plurality of connector holes within the tray, whereby the base surface is positioned proximate to an upper surface of the tray, whereby an exterior corner of at least one of the plurality of connector holes is positioned proximate to an interior corner pocket formed by the at least one fastening tab and located at least partially between the base surface and the at least one fastening tab (block 304). The bracket is retained to the tray with a retainer structure formed on the base surface of the bracket, wherein the retainer structure engages with the tray to retain the exterior corner positioned within the interior corner pocket (block 306).

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. A bracket and tray connection system comprising:
a tray having a plurality of connector holes positioned therein, wherein the tray has an upper surface and a lower surface;
a bracket having a base surface positioned proximate to an upper surface of the tray;
at least one fastening tab formed on the base surface of the bracket, wherein the at least one fastening tab extends away from the base surface and through at least one of the plurality of connector holes within the tray;
an interior corner pocket formed by the at least one fastening tab and located at least partially between the base surface and the at least one fastening tab, wherein the interior corner pocket formed by the at least one fastening tab further comprises a first planar wall and a second planar wall, the first planar wall intersecting at an angle with the second planar wall and the first and second planar walls being perpendicular to the base surface, and wherein an exterior corner of at least one of the plurality of connector holes is positioned with the interior corner pocket; and
a retainer structure formed on the base surface of the bracket, wherein the retainer structure engages with the tray to retain the exterior corner positioned within the interior corner pocket.

2. The bracket and tray connection system of claim 1, wherein at least one of the plurality of connector holes further comprises a T-shaped cutout, wherein the T-shaped cutout includes a leg portion positioned proximate to the exterior corner of the at least one of the plurality of connector holes.

3. The bracket and tray connection system of claim 1, wherein the interior corner pocket is formed by at least three intersecting surfaces of the at least one fastening tab.

4. The bracket and tray connection system of claim 1, wherein the angle is less than 180 degrees.

5. The bracket and tray connection system of claim 1, wherein the angle is substantially 90 degrees.

6. The bracket and tray connection system of claim 1, wherein the interior corner pocket further comprises at least two interior corner pockets formed by the at least one fastening tab, wherein the at least two interior corner pockets are formed on opposing sides of a central wall.

7. The bracket and tray connection system of claim 1, wherein the tray is positioned between the base surface of the bracket and a top wall of the at least one fastening tab.

8. The bracket and tray connection system of claim 1, wherein the retainer structure further comprises a positive ramp extending from the base surface.

9. The bracket and tray connection system of claim 8, wherein the positive ramp engages with a rear wall of the at least one of the plurality of connector holes and the at least one fastening tab engages with the exterior corner positioned on a front of the at least one of the plurality of connector holes.

10. The bracket and tray connection system of claim 1, wherein the retainer structure further comprises a flexible tab extending from the base surface of the bracket.

11. The bracket and tray connection system of claim 10, wherein the tray further comprises a retainer hole, wherein the flexible tab engages with the retainer hole.

12. The bracket and tray connection system of claim 11, wherein the retainer hole is separate from each of the plurality of connector holes.

13. The bracket and tray connection system of claim 1, wherein the retainer structure further comprises a negative ramp extending into the base surface.

14. The bracket and tray connection system of claim 13, wherein the negative ramp engages with a retainer tab extending from a sidewall of the at least one of the plurality of connector holes, wherein the retainer tab extends past the upper surface of the tray.

15. A bracket for supporting instruments on a tray, the bracket comprising:
   a base and an instrument holding portion extending from the base;
   a base surface positioned on an opposing side of the base from the instrument holding portion;
   at least one fastening tab formed on the base surface, wherein the at least one fastening tab extends away from the base surface;
   an interior corner pocket formed by the at least one fastening tab and located at least partially between the base surface and the at least one fastening tab, wherein the interior corner pocket formed by the at least one fastening tab further comprises a first planar wall and a second planar wall, the first planar wall intersecting at an angle with the second planar wall and the first and second planar walls being perpendicular to the base surface; and
   a retainer structure formed on the base surface.

16. The bracket for supporting instruments on a tray of claim 15, wherein the interior corner pocket further comprises at least two interior corner pockets formed by the at least one fastening tab, wherein the at least two interior corner pockets are formed on opposing sides of a central wall.

17. The bracket for supporting instruments on a tray of claim 15, wherein the retainer structure further comprises at least one of:
   a positive ramp extending from the base surface;
   a flexible tab extending from the base surface; and
   a negative ramp extending into the base surface.

18. A method of securing a bracket to a tray, the method comprising the steps of:
   providing a tray having a plurality of connector holes positioned therein, wherein the tray has an upper surface and a lower surface;
   engaging a bracket to at least one of the plurality of connector hole of the tray, the bracket having a base surface and at least one fastening tab formed on the base surface of the bracket, wherein the at least one fastening tab extends away from the base surface and through at least one of the plurality of connector holes within the tray, whereby the base surface is positioned proximate to the upper surface of the tray, whereby an exterior corner of at least one of the plurality of connector holes is positioned proximate to an interior corner pocket formed by the at least one fastening tab and located at least partially between the base surface and the at least one fastening tab, and wherein the interior corner pocket formed by the at least one fastening tab further comprises a first planar wall and a second planar wall, the first planar wall intersecting at an angle with the second planar wall and the first and second planar walls being perpendicular to the base surface; and
   retaining the bracket to the tray with a retainer structure formed on the base surface of the bracket, wherein the retainer structure engages with the tray to retain the exterior corner positioned within the interior corner pocket.

19. The method of claim 18, wherein the interior corner pocket further comprises at least two interior corner pockets formed by the at least one fastening tab, wherein the at least two interior corner pockets are formed on opposing sides of a central wall.

20. The method of claim 18, wherein retaining the bracket to the tray with the retainer structure further comprises at least one of:
   engaging a rear wall of the at least one of the plurality of connector holes with a positive ramp extending from the base surface;
   engaging the rear wall of the at least one of the plurality of connector holes with a flexible tab extending from the base surface; and
   engaging a retainer tab extending from a sidewall of the at least one of the plurality of connector holes with a negative ramp extending into the base surface.

* * * * *